(12) United States Patent
Scalone et al.

(10) Patent No.: US 6,222,039 B1
(45) Date of Patent: Apr. 24, 2001

(54) PROCESS FOR THE PREPARATION OF CHIRAL LACTONES

(75) Inventors: Michelangelo Scalone, Birsfelden; Ulrich Zutter, Basel, both of (CH)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 09/349,296

(22) Filed: Jul. 7, 1999

(30) Foreign Application Priority Data

Jul. 13, 1998 (EP) .................................................. 98112951

(51) Int. Cl.$^7$ ...................... C07D 401/06; C07D 405/06; C07D 211/20; C07D 211/60; C07D 233/72

(52) U.S. Cl. .......................... 546/210; 546/214; 546/245; 546/248; 548/316.1; 548/319.5

(58) Field of Search ...................... 546/210, 214, 546/245, 248; 548/316.1, 319.5

(56) References Cited

U.S. PATENT DOCUMENTS

| | | | |
|---|---|---|---|
| 4,556,740 | 12/1985 | Hansen et al. | 568/13 |
| 5,171,892 | 12/1992 | Burk | 568/12 |
| 5,274,125 | 12/1993 | Broger et al. | 549/216 |
| 5,288,928 | 2/1994 | Broger et al. | 568/807 |
| 5,371,256 | 12/1994 | Togni et al. | 556/14 |
| 5,430,191 | 7/1995 | Foricher et al. | 568/12 |
| 5,457,219 | 10/1995 | Foricher et al. | 556/404 |
| 5,463,097 | 10/1995 | Togni et al. | 556/14 |
| 5,466,844 | 11/1995 | Spindler et al. | 556/11 |
| 5,481,008 | 1/1996 | Broger et al. | 549/292 |
| 5,488,172 | 1/1996 | Cereghetti et al. | 568/13 |
| 5,563,308 | 10/1996 | Spindler et al. | 585/277 |
| 5,563,309 | 10/1996 | Togni et al. | 585/277 |
| 5,565,594 | 10/1996 | Spindler et al. | 556/28 |
| 5,583,241 | 12/1996 | Spindler | 556/11 |
| 5,614,625 | 3/1997 | Broadhurst et al. | 540/480 |
| 5,698,690 | 12/1997 | Broadhurst et al. | 540/480 |
| 5,710,167 | 1/1998 | Broadhurst et al. | 514/326 |
| 5,731,441 | 3/1998 | Broadhurst et al. | 285/10 |
| 5,750,690 | 5/1998 | Broger et al. | 544/234 |
| 5,852,212 | 12/1998 | Broger et al. | 562/602 |
| 5,952,507 | 9/1999 | Hilpert | 546/226 |

FOREIGN PATENT DOCUMENTS

| | | |
|---|---|---|
| 197 06 273 | 7/1997 | (DE) . |
| 104 375 | 4/1984 | (EP) . |
| 398 132 | 11/1990 | (EP) . |
| 492 401 | 7/1992 | (EP) . |
| 564 406 | 10/1993 | (EP) . |
| 570 764 | 11/1993 | (EP) . |
| 612 758 | 8/1994 | (EP) . |
| 643 052 | 3/1995 | (EP) . |
| 646 590 | 11/1995 | (EP) . |
| 684 240 | 11/1995 | (EP) . |
| 749 953 | 12/1996 | (EP) . |
| 816 341 | 1/1998 | (EP) . |
| WO 92 16536 | 10/1992 | (WO) . |

OTHER PUBLICATIONS

Compagnone et al., Synthetic Communications, vol. 22, No. 21, 1992, pp. 3041–3051.

Momose et al., Chem. Pharm. Bull., vol. 40, No. 9, 1992, pp. 2525–2530.

Borne et al., J. Med. Chem., vol. 16, 1973, pp. 245–247.

Szepesi et al., Pharmazie, vol. 38, No. 2, 1983, pp. 94–98.

Bundgaard et al., J. Pharm. Sci., vol. 75, No. 1, 1986, pp. 36–43.

Patrick Lesimple, Dennis C.H. Bigg, *Aluminum Chloride Mediated Aminolysis of Lactones: A General Method for the Preparation of ω–Hydroxyalkylamides*, pp. 306–308, 1991.

Primary Examiner—Ba K. Trinh
(74) Attorney, Agent, or Firm—George W. Johnston; William H. Epstein

(57) ABSTRACT

The present invention relates to a process for the preparation of compounds of formula I

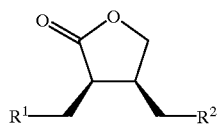

(I)

wherein $R^1$ and $R^2$ are as defined in the specification as well as to the novel intermediates obtained by said process.

5 Claims, No Drawings

PROCESS FOR THE PREPARATION OF CHIRAL LACTONES

The present invention is concerned with a novel process for the manufacture of intermediates which are useful in the synthesis of pharmacologically active compounds. The invention also relates to the novel intermediates obtained in said process which are useful in the synthesis of pharmacologically active compounds.

DESCRIPTION OF THE INVENTION

In one aspect, the invention is concerned with a process for the manufacture of a lactone having the formula I

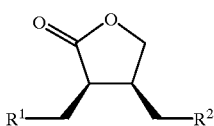

(I)

wherein $R^1$ signifies lower alkyl or lower cycloalkyl and $R^2$ represents a 5- or 6-membered N-heterocyclic ring which (a) is attached via the N atom, (b) optionally contains N, O and/or S, SO or $SO_2$ as an additional ring member, (c) is substituted by oxo on one or both C atoms adjacent to the linking N atom and (d) is optionally benz-fused or optionally substituted on one or more other C atoms by lower alkyl or oxo and/or on any additional N atom(s) by lower alkyl.

In accordance with the invention compounds of formula (I) can be manufactured by hydrogenating asymmetrically a compound of formula (II)

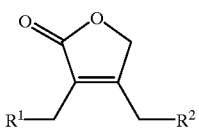

(II)

wherein $R^1$ and $R^2$ have the meaning as given before, in the presence of an optically active metal diphosphine complex.

As used in this specification, the term "lower alkyl", alone or in combination, means a straight-chain or branched-chain alkyl group containing a maximum of six carbon atoms, such as methyl, ethyl, n-propyl, isopropyl, n-butyl, sec.butyl, isobutyl, tert.butyl, n-pentyl, n-hexyl and the like.

The term "lower cycloalkyl" means a cycloalkyl group containing 3 to 6 carbon atoms, i.e. cyclopropyl, cyclobutyl, cyclopentyl and cyclohexyl.

Examples of N-heterocyclic rings denoted by $R^2$ are rings of the formula:

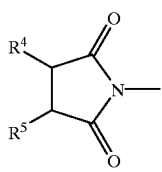

(a)

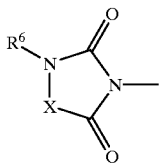

(b)

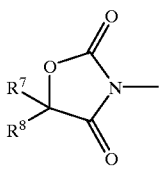

(c)

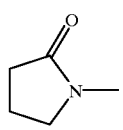

(d)

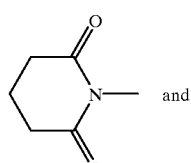

(e)

and

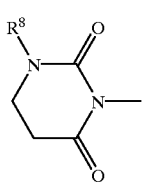

(f)

wherein $R^4$ and $R^5$ each represent hydrogen or together represent an additional bond or the remainder of a fused benzene ring;

$R^6$ represents hydrogen or lower alkyl;

X represents —CO—, —$CH_2$—, —CH(lower alkyl)—, —C(lower alkyl)$_2$—, —NH—, —N(lower alkyl)— or —O—; and $R^7$ and $R^8$ each represent hydrogen or lower alkyl.

Examples of such rings are 2-oxo-1-pyrrolidinyl, 2,5-dioxo-1-pyrrolidino, phthalimido, 1,2-dimethyl-3,5-dioxo-1,2,4-triazolidin-4-yl, 3-methyl-2,5-dioxo-1-imidazolidinyl, 3,4,4-trimethyl-2.5-dioxo-imidazolidin-1-yl, 2-methyl-3,5-dioxo-1,2,4-oxadiazol-4-yl, 3-methyl-2,4,5-trioxo-1-imidazolidinyl and 2,6-dioxopiperidino.

Preferred rings are those of formula (a), (b) or (c) with formula (b) being most preferred. Within formula (b) a preferred substituent is 3,4,4-trimethyl-2,5-dioxo-imidazolidin-1-yl.

A preferred group within $R^1$ is lower cycloalkyl with cyclopentyl being most preferred.

Although the formulas presented herein show the respective compounds in their absolute stereochemistry, the invention embraces not only the depicted stereoisomers of a compound of formula (I), but also the corresponding enantiomers. The same applies to the products which can be made out of these compounds.

In one embodiment the asymmetric hydrogenation can be carried out using complexes of optically active, preferably atropisomeric, diphosphine ligands with a metal of Group VIII of the periodic system, especially rhodium, as the catalyst. Complexes which can be used as catalysts in the process of the present invention are

  (III)

wherein

L signifies a neutral ligand

A signifies an anion of an oxygen or complex acid n signifies 0, 1 or 2

Y signifies an optically active, preferably atropisomeric diphosphine ligand.

The term "neutral ligand" signifies in the scope of the present invention readily exchangeable ligands such as olefins, e.g. ethylene, propylene, cyclooctene, 1,5-hexadiene, 1,5-cyclooctadiene and the like, nitriles such as acetonitrile and benzonitrile or also the solvent which is used. Where more than one such ligand is present, they can be the same or different from each other.

The term "oxygen acid" signifies in the scope of the present invention acids from the group $H_2SO_4$, $HClO_4$, $HBrO_4$, $HIO_4$, $HNO_3$, $H_3PO_4$, $CF_3SO_3H$ or $C_6H_5SO_3H$. The term "complex acid" signifies in the scope of the present invention halogen complexes with the elements boron, phosphorus, arsenic, antimony or bismuth. $HClO_4$, $CF_3SO_3H$, $HPF_6$, $HBF_4$, $HB(Ph)_4$, $HB(3,5-(CF_3)_2-C_6H_3)_4$, $HSbF_6$ and $HAsF_6$ are preferred representatives with $HSbF_6$ and $HBF_4$ being most preferred.

Suitable chiral ligands Y in the chiral diphosphin-complexes, which can exist in the (R) or (S) form, can be selected from the group consisting of:

| | |
|---|---|
| MeOBIPHEP: | (6,6'-Dimethoxybiphenyl-2,2'-diyl)bis-(diphenylphosphine) |
| BIPHEMP: | (6,6'-Dimethylbiphenyl-2,2'-diyl)bis-(diphenylphosphine) |
| BINAP: | [(1,1'-Binaphthyl)-2,2'-diyl]bis-(diphenylphosphine) |
| 2-Furyl-MeOBIPHEP: | (6,6'-Dimethoxybiphenyl-2,2'-diyl)bis(di-2-furylphosphine) |
| 2-Naphthyl-MeOBIPHEP: | (6,6'-Dimethoxybiphenyl-2,2'-diyl)bis(di-2-naphthylphosphine) |
| TriMeOBIPHEP: | (4,4',5,5',6,6'-Hexamethoxybi-phenyl-2,2'-diyl)bis(diphenylphosphine) |
| (3,5-Me,4-MeO)-MeOBIPHEP: | (6,6'-Dimethoxybiphenyl-2,2'-diyl)bis[bis(3,5-dimethyl-4-methoxy-phenyl)phosphine] |
| Me-DuPHOS: | 1,2-Bis(2,5-dimethylphospho-lano)benzol |
| 3,5-iPr-MeOBIPHEP: | (6,6'-Dimethoxybiphenyl-2,2'-diyl)bis[bis(3,5-diiso-propyl-phenyl)phosphine] |
| PPF-P(tBu)$_2$: | 1-[2-(Diphenylphosphino)fer-rocenyl]ethyl-di-tert.-butyl-phosphine |
| pCF$_3$-PPF-PPh$_2$: | 1-[2-(Di-(4-trifluoromethyl)phenyl)-phosphino)ferrocenyl]ethyl-di-phenyl-phosphine |
| 3,5-tBu$_2$-MeOBIPHEP: | P,P-Bis-(3,5-di-tert-butyl-phenyl)-P'P'-diphenyl-(6,6'-dimethoxybi-phenyl-2,2'-diyl)diphosphine |
| (3,4,5-MeO)-MeOBIPHEP: | (6,6'-Dimethoxybiphenyl-2,2'-diyl)bis(di-3,4,5-trimethoxy-phenyl)phosphine) |

These ligands are known and/or can be prepared according to the Examples or methods as described in EP O 398 132 A2 and WO-92/16535 (MeOBIPHEP; TriMeOBIPHEP, 3,5-iPr-MeOBIOPHEP, 3,5-tBu$_2$-MeOBIPHEP, (3,4,5-MeO)-MeOBIPHEP, (3,5-Me, 4-MeO)-MeOBIPHEP, 2-Naphtyl-MeOBIPHEP), EP O 104 375 A1(BIPHEMP), EP O 580 331 A1 (BINAP), WO 92/16536 (2-Furyl-MeOBIPHEP), U.S. Pat. No. 5,171,892 (Me-DuPHOS), EP O 564 406 A1 (PPF-P(tBu)$_2$), and EP O 646 590 A1 (pCF$_3$-PPF-PPh$_2$).

The preferred optically active rhodium complexes (III) can be synthesized or prepared in situ from the components in the absence or in the presence of the compounds of formula II to be hydrogenated. The optically active rhodium diphosphine complexes are either known or can be produced in a manner known per se, e.g. by reacting an optically active atropisomeric diphosphine ligand Y described above with a compound which can yield rhodium in a suitable inert organic or aqueous solvent. As suitable compounds which yield rhodium there can be mentioned, for example, organic rhodium complexes with ethylene, propylene and the like and with dienes, e.g. (Z,Z)-1,5-cyclooctadiene, 1,5-hexadiene and bicyclo[2.2.1]hepta-2,5-diene, which form readily soluble complexes with rhodium. Preferred compounds which yield rhodium are e.g. di-$\mu$-chloro-bis[$\eta^4$-(Z,Z)-1,5-cyclooctadiene]dirhodium(I), di-$\mu$-chloro-bis[$\eta^4$-norbornadiene]dirhodium(I), di-$\mu$-trifluoroacetato-bis[$\eta^4$-(Z,Z)-1,5-cyclooctadiene]dirhodium(I), bis[$\eta^4$-(Z,Z)-1,5-cyclooctadiene]rhodium(I) tetrafluoroborate, bis[$\eta^4$-(Z,Z)-1,5-cyclooctadiene]rhodium(I) perchlorate and bis[$\eta^4$-(Z,Z)-1,5-cyclooctadiene]rhodium(I) hexafluoroantimonate. Other metal catalysts with e.g. iridium can be prepared in the same manner.

The ratio of rhodium to Ligand Y in the complexes of formula (III) conveniently lies between about 0.5 and about 2 mol, preferably at about 1 mol, of rhodium per mol of ligand. The substrate/catalyst ration (S/C; mol/mol) conveniently lies between about 20 and about 20000, preferably between about 100 and about 5000.

In the method of the present invention [(Rh(1,5-Cyclooctadiene)((R)-3,5-iPr-MeOBIPHEP)](SbF$_6$) is an especially preferred catalyst. For obtaining a compound with the absolute stereochemistry as shown in Formula I (i.e. (R,R)) a ligand Y of the atropisomeric type having the (R) form is used. For obtaining the enantiomer of a compound of formula I a complex with an atropisomeric ligand having the opposite (S) stereochemistry is used. Accordingly, the preparation of such enantiomers is also encompassed by the process of the present invention.

Conveniently, the hydrogenation is carried out with the exclusion of oxygen in a suitable solvent such as an ester, e.g. ethyl acetate, an ether, e.g. THF or a halogenated hydrocarbon, e.g. $CH_2CH_2$ Supercritical or liquid $CO_2$ may also be used alone or in a mixture with a solvent. A preferred solvent is ethyl acetate under an elevated pressure, e.g. at pressures of 1 to 300 bar, preferably 40 to 100 bar, and at temperatures of 40 to 180° C., preferably 60°–100° C.

The compounds of formula II, wherein $R^2$ is a 5- or 6 membered N-heterocyclic ring can be prepared according to the following reaction scheme A.

Reaction Scheme A

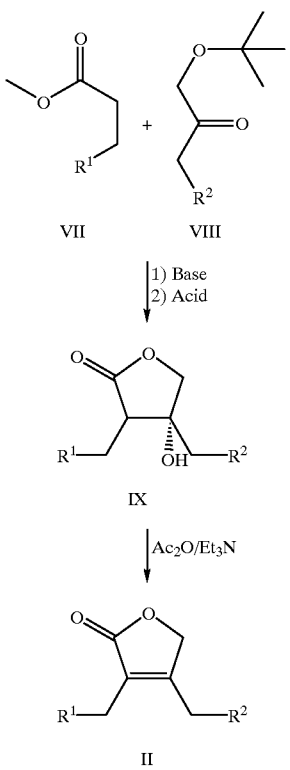

Having regard to Reaction Scheme A, in the first step an ester of formula (VII) is reacted with a compound of formula (VIII) by firstly deprotonizing the ester (VII) with a base, preferably lithium diisopropyl amine (LDA) in a solvent such as an ether, e.g. THF, at a temperature of 0° to –80° C., preferably –75°, and then reacting the keton VIII with the esterenolate of (VII) in the same solvent. After acidification with a mineral acid, preferably $H_2SO_4$, the reaction mixture is heated to afford after deprotection and cyclization lactone (IX).

In the next step a compound of formula (IX) is dehydrated with a strong acid such as conc. $H_2SO_4$ or with an acid chloride, e.g. acetyl chloride, or an anhydride, e.g. acetic anhydride, and a sterically hindered base such as an tertiary amine, e.g. triethylamine, at a temperature of 0° to 100° C., preferably about 90° C., to yield a compound of formula I.

The esters of formula (VII) are known compounds. They can be either purchased or can be prepared in a known manner via esterification of the corresponding known acids. Compounds of formula VII in which $R^1$ is methyl, ethyl or propyl can be purchased from Fluka. Compounds of formula VII in which $R^1$ is isopropyl or cyclohexyl can be purchased from Aldrich. 3-cyclopentyl-propionic acid methylester was purchased from Chemische Fabrick K. Bücher Germany. Alternatively, any conventional esterification reaction can be used to form the compounds of formula VII from the corresponding acid, for example by treatment with methanol/conc. $H_2SO_4$.

Amine compounds of formula $HR^2$ are commercially available or can be synthesized using reactions that are conventional in the organic chemistry field. Examples of commercially available compounds of formula $HR^2$ include: phthalimide (Aldrich P3, 970-2); 1,1,5-trimethylhydantoin (Aldrich 47, 940-3); 1-methylhydantoin (Aldrich M4, 988-7); 2-pyrrolidone (Aldrich P7, 437-0); succinimide (Aldrich S555-3); glutarimide (Aldrich 17, 809-8); maleimide (Aldrich 12, 958-5); 5,6-dihydrouracil (Aldrich 21, 964-9); 5,6-dihydro-1-ethyluracil (Salor 593, 269-9); 5-6-dihydro-1-methyluracil (Salor S10, 851-0); 5,5-dimethyl-2,4-oxazolidine (Aldrich 21, 900-2); 2,4-thiazolidinedione (Aldrich 37,500-4); and saccharin (Aldrich 10, 918-5).

Compounds of Structure

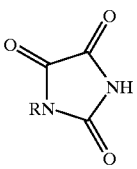

are be prepared by the method of H. Ulrich and A. A. R. Sayigh, J.Org.Chem., 1965, 30, 2781 but by using dimethylformamide as solvent in place of ethylene dichloride.

Compounds of Structure

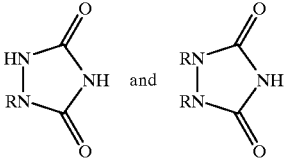

are prepared by conventional adaptation of methods disclosed in the following:

M. J. Bausch et al. J. Org. Chem., 1991, 56, 5643; Z. Gerwalt and G. Isensee, Chem.-Ztg., 1973, 97(2), 73. (CAN 78: 13,5601); JP 76-128713, (CAN 89:197555); and U.S. 70-701016, (CAN 78:72175).

Compounds of Structure

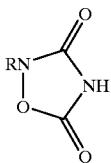

are prepared by conventional adaptation of methods disclosed by B. W. Bycroft et al. in J.Chem. Soc. Chem. Commun., 1984, 1156.

The preparation of related compounds of formula $HR^2$ should be achievable by those skilled in the art using adaptations of the methods given in the above references.

Compounds of formula (VIII), wherein $R^2$ is a 5- or 6 membered N-heterocyclic ring, can be prepared by reacting (RS)-2-tert-Butoxymethyl-oxirane with the free amine $HR^2$ in a known manner. The amine is dissolved in a solvent such as DMF or $H_2O$ and treated with the oxirane in the presence of catalytic amounts of a base, such as KOH, NaOH or NaH, at a temperature of 0°–90° C. Then the alcohol intermediate is oxidized to the corresponding ketone using known oxidizing agents such as NaOCl, KBr and catalytic amounts of 2,2,6,6-tetramethyl-piperidin-1-oxyl (TEMPO).

The compounds of formula (I) can be converted into compounds of formula (Ia) wherein the corresponding $R^1$ and $R^2$ substituents are trans oriented.

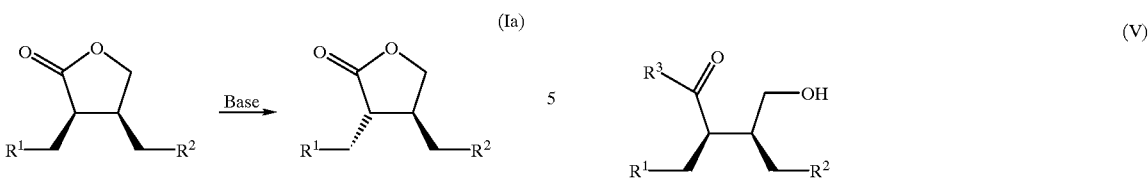

(Ia)

This epimerization can be done by treating a compound of formula (I) in a suitable solvent such as an ether, e.g. THF, or an ester, e.g. ethyl acetate, with a base such as 1,8-Diazabicyclo[5.4.0]undec-7-ene(1,5-5) (DBU) at increased temperature. The enantiomer of a compound of formula (Ia) can be prepared starting with the enantiomer of a compound of formula (I).

Another object of the present invention is the synthesis of compounds of formula (IV)

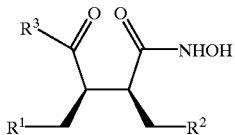

(IV)

wherein $R^1$, $R^2$ are as defined before and $R^3$ represents a saturated 5- to 7-membered monocyclic N-heterocyclic ring which is attached via the N-atom and optionally contains $NR^4$ or O as a ring member and $R^4$ represents hydrogen, lower alkyl, aryl, aralkyl or a protecting group.

In this connection, the term "aryl" means phenyl which is optionally substituted by, for example, lower alkyl, lower alkoxy and/or halogen, i.e. fluorine, chlorine, bromine or iodine, such as p-tolyl, p-methoxyphenyl, p-chlorophenyl and the like. The term "aralkyl" means a lower alkyl group as hereinbefore defined in which one or more hydrogen atoms is/are replaced by an aryl group as hereinbefore defined, such as benzyl and the like.

A protecting group denoted by $R^4$ can be any conventional protecting group, e.g. as known in peptide chemistry such as benzyloxycarbonyl, tert.butoxycarbonyl, acetyl and the like.

Examples of monocyclic N-heterocyclic rings denoted by $R^3$ are 1-pyrrolidinyl, piperidino, 1-piperazinyl, 4-aryl-1-piperazinyl, hexahydro-1-pyridazinyl, morpholino and hexahydroazepino which can be substituted in the manner given earlier. Examples of substituted rings are 4-methyl-1-piperazinyl or 4-phenyl-1-piperazinyl. Preferably $R^3$ is piperidino.

Compounds of formula (IV) are described in European patent application publication No. 0 684 240 A1. These compounds having the stereochemistry shown above are inhibitors of matrix metalloproteinases and can be used in the control or prevention of illnesses, especially in the control or prevention of degenerative joint diseases such as rheumatoid arthritis and osteoarthritis or in the treatment of invasive tumors, atherosclerosis or multiple sclerosis.

The compounds of formula (IV) can be prepared using the compounds of formula (I) prepared as described before. The process is characterized in that a) a compound of formula (I) is reacted with a cyclic amine $HR^3$ yielding a compound of formula (V)

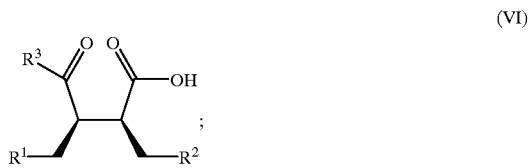

(V)

wherein $R^1$, $R^2$ and $R^3$ are as defined before for compounds of formula IV;

b) oxidizing the hydroxyl group in a compound of formula (V) and obtaining a compound of formula (VI)

(VI)

c) converting the compound of formula (VI) into a compound of formula IV by introducing a hydroxyl amine group; and d) optionally removing any protecting group $R^4$.

The amide formation from the lactone of formula (I) in step a) with the cyclic amine $HR^3$ to give a compound of formula (V) can be effected according to methods known per se, such as e.g. reacting an excess of the amine with a compound of formula (I) in a hydrocarbon, e.g. toluene at 25° to 120°, or in a halogenated hydrocarbon, e.g. methylene chloride, in the presence of a Lewis acid like $AlCl_3$ at a temperature of 0° to 50°, preferably 0° to 25°.

The oxidation of the hydroxy group in a compound of formula (V) to a compound of formula (VI) mentioned in step b) is effected via known mild oxidation methods using, e.g. NaOCl, KBr and 2,2,6,6-Tetramethyl-piperidin-1-oxyl.

The introduction of the hydroxylamine group in step c) can be effected by means of O-trimethylsilylhydroxylamine with activating agents known per se, such as carbodiimides, e.g. dicyclohexylcarbodiimide, or an isocyanide, e.g. t-butyl isocyanide, preferably 2-morpholino-ethyl isocyanide, in the presence of stoichiometric or catalytic amounts of alcohols which form active esters, such as e.g. N-hydroxysuccinimide, N-hydroxybenzotriazole or preferably N-hydroxy-2-pyridone, in a solvent such as an ether, e.g. t-butyl methyl ether, or a hydrocarbon, e.g. toluene, or a halogenated hydrocarbon or an ester, preferably methylene chloride or, respectively, ethyl acetate at a temperature of 0 to 80°, preferably 10 to 25°.

Removal of any protecting group $R^4$ can be performed by methods known per se. Basic compounds of formula (IV) may be converted into pharmaceutically acceptable salts by treatment with acids. Such treatments can be carried out in a conventional manner.

In the same manner as described for the conversion of compounds of formula (I) into compounds of formula (IV), compounds of formula (Ia) can be converted into compounds of formula (IVa)

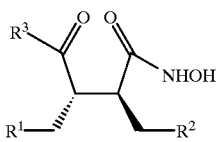

(IVa)

wherein R¹, R² and R³ are as defined before.

The same conversion can be done with the enantiomer of a compound of formula (Ia) to obtain the enantiomer of a compound of formula (IVa).

Another object of the present invention are the novel intermediates obtained. In particular these are Compounds of Formula (I)

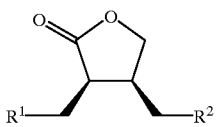

(I)

wherein R¹ and R² are as defined before, especially (3R,4R)-3-(4-Cyclopentylmethyl-5-oxo-tetrahydrofuran-3ylmethyl)-1,5,5-trimethyl-imidazolidine-2,4-dione;

Compounds of Formula II

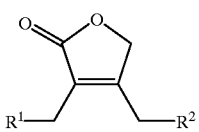

(II)

wherein R¹ and R² are as defined before, especially 3-(4-Cyclopentylmethyl-5-oxo-2,5-dihydro-furan-3ylmethyl)-1,5,5-trimethyl-imidazolidine-2,4-dione;

Compounds of Formula V

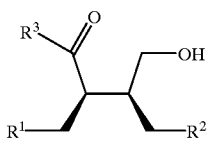

(V)

wherein R¹, R² and R³ are as defined before, especially (2R,3R)-3-(3-Cyclopentylmethyl-2-hydroxymethyl-4-oxo-4-piperidin-1-yl butyl)-1,5,5-trimethyl-imidazolidine-2,4-dione.

These compounds are especially suitable in the preparation of compounds of formula IV in particular of (2R,3R)-3-Cyclopentylmethyl-N-hydroxy-4-oxo-4-piperidin-1-yl-2-(3,4,4-trimethyl-2,5-dioxo-imidazolidin-1-ylmethyl)-butyramide. This means that a compound of formula (I), wherein R¹ is cyclopentyl and R² is 3,4,4-trimethyl-2,5-dioxo-imidazolidin-1-yl, is reacted in step a) with piperidin followed by oxidization in step b) and introduction of the hydroxylamine group in step c).

The contents of European Patent Application No. 98112951.3, filed Jul. 13, 1998 are incorporated herein by reference.

The invention is now described by way of some examples without limiting it to them. In the Examples the following abbreviations have been used:

| | |
|---|---|
| ee | enantiomeric excess (determind by HPLC as described) |
| GC | gas chromatography (on fused silica) for determining the amount of product obtained |
| h | hours |
| HPLC | High Performance Liquid Chromatography |
| MS (ISP,EI) | Mass Spectroscopy (ISP: Ion Spray positive; EI: Electron Ionization) |
| r.t. | room temperature |
| mp. | melting point |
| THF | tetrahydrofuran |
| COD | 1,5-cyclooctadiene |
| Conv./h | % conversion/reaction time in hours |
| $CO_{2SC}$ | supercritical $CO_2$ |

All temperatures are given in degrees Celsius

EXAMPLES

Example 1

3-(3-tert-Butoxy-2-oxo-propyl)-1,5,5-trimethyl-imidazolidine-2,4-dione

To 500 ml deionized water were added 5.6 g potassium hydroxide (0.1 mole), 71.1 g 1,5,5-trimethyl-imidazolidine-2,4-dione (H. Heimgartner et al, Helv. Chem. Acta (1992) 75, 1251) and 78.1 g (RS)-2-tert-Butoxymethyl-oxirane (Fluka No. 19941) and the reaction mixture was heated to 70°. After stirring for 4 h the reaction mixture was cooled down to r.t. Afterwards, 20.0 g potassium bicarbonate, 11.2 ml 48% hydrobromic acid (ca. 0.1 mole) and 500 ml dichloromethane were added and the reaction mixture was cooled down to 0°. After the addition of 0.4 g 2,2,6,6-tetramethyl-piperidin-1-oxyl (TEMPO, Aldrich No. 21400) 472 g 10.5% aqueous sodium hypochlorite were added under vigorous stirring at 0° over 2 h. After additional stirring at 0° for 0.5 h, the excess of NaOCl was destroyed by the addition of ca. 10 ml 38% aqueous sodium bisulfite and the reaction mixture was warmed up to r.t. The aqueous layer was separated and extracted with dichloromethane. Both organic layers were washed with 10% brine, combined and dried over sodium sulfate.

After filtration and evaporation of the solvent, the oily residue (143 g) was dissolved in 500 ml methylcyclohexane at 60°, seeded with pure 3-(3-tert-butoxy-2-oxo-propyl)-1,5,5-trimethyl-imidazolidine-2,4-dione, cooled down to 0° over 2 h and stirred at −10° for 4 h. The crystal suspension was filtered, washed with cold methylcyclohexane and dried over night under reduced pressure affording 122.8 g (90.9%) of white 3-(3-tert-butoxy-2-oxo-propyl)-1,5,5-trimethyl-imidazolidine-2,4-dione, mp. 61–63° C.

$C_{13}H_{22}N_2O_4$ (270,329) Calcd. C, 57.76; H, 8.20; N, 10.36. Found C, 57.73; H, 8.18; N, 10.46.

Example 2

3-(4-Cyclopentylmethyl-3-hydroxy-5-oxo-tetrahydrofuran-3-ylmethyl)-1,5,5-trimethyl-imidazolidine-2,4-dione 203 ml 1.6M Butyllithium in hexane were added to a solution of 46.0 ml diisopropylamine in 120 ml THF at 0° over 1 h. The resultant LDA-solution was stirred at 0° for 1 h and then cooled down to −75°. 50.8 g 3-cyclopentyl-propionic acid methylester dissolved in 65 ml THF were added at −75° over 1 h and stirring at that temperature was continued for 1 h. 67.6 g 3-(3-tert-butoxy-2-oxo-propyl)-1,5,5-trimethyl-imidazolidine-2,4-dione dissolved in 65 ml THF were added at −75° over 1 h and after additional stirring at −75° for 1 h, 50 ml conc. $H_2SO_4$ were added over 15 minutes. The reaction mixture was refluxed for 3 h, cooled down to r.t. and hydrolyzed with 300 ml deionized water. The organic layer was separated, washed with 10% brine and dried over $Na_2SO_4$. Filtration and evaporation of the solvent afforded 96.5 g crude 3-(4-cyclopentylmethyl-3-hydroxy-5-oxo-tetrahydro-furan-3-ylmethyl)-(1,5,5-trimethyl-imidazolidine-2,4-dione as a yellow oil, which was used without purification for the next step. 3-Cyclopentyl-propionic acid methylester was prepared from the corresponding acid (ACROS No. 11161). The methylester is also available at Chemische Fabrik K. Bucher.

Example 3

3-(4-Cyclopentylmethyl-5-oxo-2,5-dihydro-furan-3ylmethyl)-1,5,5-trimethyl-imidazolidine 2,4-dione To a solution of 96.5 g crude product obtained in Example 2 in 250 ml acetic anhydride were added 175 ml triethylamine all at once and the reaction mixture was stirred at 90° for 14 h. The oil bath was removed and 150 ml ethanol were added first over 0.5 h and then 100 ml 37% HCl over 15 minutes. After cooling down to r.t., the reaction mixture was diluted with 250 ml ethyl acetate and washed 3× with deionized water. All aqueous layers were extracted sequentially with 100 ml ethyl acetate. The combined organic layers were stirred with 25 g $Na_2SO_4$ and 8 g charcoal (Darco G60 Fluka No. 5100) for 0.5 h. Filtration over Hyflo Super Cel® (Fluka No.56678) and evaporation of the solvent afforded 96.5 g crude, viscous 3-(4-cyclopentylmethyl-5-oxo-2,5-dihydro-furan-3ylmethyl)-1,5,5-trimethyl-imidazolidine-2,4-dione, which was dissolved in 400 ml diisopropyl ether at 500, cooled down to -20° over 2 h and stirred over night. The crystal suspension was filtered, washed with cold diisopropyl ether and dried under reduced pressure to afford 71,2 g beige 3-(4-cyclopentylmethyl-5-oxo-2,5-dihydro-furan-3ylmethyl)-1,5,5-trimethyl-imidazolidine-2,4-dione, mp. 77–79°. The product can be further purified by a second cristallisation step, mp. 78.5–79.5°.

$C_{17}H_{24}N_2O_4$ (320,389) Calcd. C, 63.63; H, 7.55; N, 8.74. Found: C, 63.76; H, 7.45; N, 8.75.

Example 4a (3RS,4RS)-3-(4-Cyclopentylmethyl-5-oxo-tetrahydrofuran-3ylmethyl)-1,5,5-trimethyl-imidazolidine-2,4-dione 19. 2 g of the product obtained in Example 3 dissolved in 120 ml ethyl acetate were hydrogenated at r.t. over 7.7 g 5% Rh—$Al_2O_3$ for 18 h. Removal of the catalyst by filtration over ca.3 g Hyflo Super Cel® (Fluka No. 56678) followed by evaporation of the solvent yielded 19.2 g of viscous oil, which was dissolved in 120 ml diisopropyl ether at 65°. Crystallization afforded 17.7 g (91.9%) white (3RS,4RS)-3-(4-cyclopentylmethyl-5-oxo-tetrahydrofuran-3ylmethyl)-1,5,5-trimethyl imidazolidine-2,4-dione, mp. 71–74°, which contained ~8% of the trans-isomer.

The pure cis (3RS,4RS)-3-(4-cyclopentylmethyl-5-oxo-tetrahydrofuran-3ylmethyl)-1,5,5-trimethyl imidazolidine-2,4-dione was obtained by chromatographic purification on silica gel (hexane:EtOAc=3:2) followed by crystallization from diisopropyl ether (mp.=75–76°).

MS (ISP) M/z 340.2 ($M+NH_4^+$), 323.3 ($M+H^+$);
$^1$H-NMR ($CDCl_3$) δ2.90 (m, 1H, C(4)-H), 2.70 (m, 1H, C(3)-H).

Example 4b (3RS,4SR)-3-(4-Cyclopentylmethyl-5-oxo-tetrahydrofuran-3ylmethyl)-1,5,5-trimethyl-imidazolidine-2,4-dione The trans compound was prepared from the cis as follows: Under an inert Argon atmosphere 1.61 g (3RS,4RS)-3-(4-cyclopentylmethyl-5-oxo-tetrahydrofuran-3ylmethyl)-1,5,5-trimethyl imidazolidine-2,4-dione and 0.77 g 1,8-Diazabicyclo[5.4.0]undec-7-ene (1,5-5) (DBU) in 15 ml THF were refluxed for 19 h. The reaction mixture was diluted with 40 ml ethyl acetate and washed with 10 ml 1N HCl and with 10 ml 10% brine. The organic layer was dried over $Na_2SO_4$, filtered and evaporated. The resultant 1.54 g yellow oil were chromatographed on 100 g silica with 1000 ml hexane/EtOAc 3:2. To yield 0.70 g (43%) colourless, oily trans-epimer (3RS,4SR)-3-(4-cyclo-pentylmethyl-5-oxo-tetrahydrofuran-3ylmethyl)-1,5,5-trimethyl-imidazolidine-2,4-dione. MS (ISP) m/z 323 ($M+H^+$)
$^1$H-NMR ($CDCl_3$) δ2.70 (m, 1H, C(4)-H), 2.40 (m, 1H, C(3)-H).

Example 4c (3R,4R)-3-(4-Cyclopentylmethyl-5-oxo-tetrahydrofuran-3ylmethyl)-1,5,5-trimethyl-imidazolidine-2,4-dione In the glove box ($O_2$ content<=2 ppm) a 10 ml measuring flask was charged with 68.3 mg [Rh((R)-3,5-iPr-MeOBIPHEP)(COD)]$SbF_6$ (0.050 mmol) and filled to the graduation mark with 10 ml ethyl acetate. The suspension was stirred with a magnetic stirring bar for 15 min at r.t. A clear orange solution formed. The Rh-catalyst was prepared through reaction of (R)-3,5-iPr-MeOBIPHEP and [Rh(COD)$_2$]$SbF_6$ in THF at room temperature for 2 h in a known manner (J. Am. Chem. Soc., 93, 3089–91 (1971), J. Chem. Soc. Chem. Comm., 1990, 869–71). In the glove box a 185 ml stirred stainless steel autoclave was charged with 16.02 g 3-(4-cyclopentylmethyl-5-oxo-2,5-dihydro-furan-3ylmethyl)-1,5,5-trimethyl-imidazolidine 2,4-dione, 20 ml ethyl acetate and the above catalyst solution. The measuring flask was rinsed with a total of 11.5 ml ethyl acetate. The autoclave was then sealed and connected to a hydrogenation line. The hydrogenation was carried out while stirring at 80° C. at a total pressure of 100 bar. After 71 h the brown hydrogenation mixture was rotary evaporated and dried at 50° C./10 mbar for 2 h, affording 16.80 g of crude (3R,4R)-3-(4-cyclopentylmethyl-5-oxo-tetrahydrofuran-3ylmethyl)-1,5,5-trimethyl-imidazolidine-2,4-dione as a brown oil which solidified slowly on standing at r.t. ee: 98.2% (3R, 4R). GC:98.4 area %. This crude material was employed directly in the next step.

Analytically pure (3R,4R)-3-(4-cyclopentylmethyl-5-oxo-tetrahydrofuran-3ylmethyl)-1,5,5-trimethyl-imidazolidine-2,4-dione was obtained as follows: A solution of 6.41 g crude (3R,4R)-3-(4-cyclopentylmethyl-5-oxo-tetrahydrofuran-3ylmethyl)-1,5,5-trimethyl-imidazolidine-2,4-dione in 170 ml diisopropyl ether was heated at reflux under stirring. After the partially insoluble catalyst had been filtered off, seed crystals of pure (3R,4R)-3-(4-cyclopentylmethyl-5-oxo-tetrahydrofuran-3ylmethyl)-1,5,5-trimethyl-imidazolidine-2,4-dione were added to the solution at 50° under stirring. The heating bath was removed and cristallization was completed over night at r.t. The crystals were filtered off, washed with diisopropyl ether and dried in vacuum affording 3.84 g (60%) of pure (3R,4R)-3-(4-cyclopentylmethyl-5-oxo-tetrahydrofuran-3ylmethyl)-1,5,5-trimethyl-imidazolidine-2,4-dione as white crystals. mp.: 87.5–88.5° C., ee: 100%; GC: 99.8 area %; $[α]_D^{20}$ −21.3° (589 nm), −24.8° (546 nm) ($CHCl_3$, c=1).

A sample of the compounds obtained in Examples 4a, 4b and 4c was dissolved and separated via HPLC as follows to determine their optical purity: For HPLC analysis a sample of the pure product or of a crude reaction mixture was evaporated to dryness and the residue filtered through a short silica pad eluted with diethyl ether. After evaporation, the residue was dissolved in 1 ml of ethyl acetate and analyzed via HPLC. Column: 2×Chiralcel OD-H, (250×4 mm), Daicel Chemicals Industries, LTD. Cat. No. 7482-00; Mobile phase: 15% (v/v) ethanol in n-hexane; Flow 1.0 ml/min; Pressure 80 bars. The following retention times were observed: 18.39 min. trans (3S,4R); 19.29 min. cis (3S,4S); 21.07 min. cis (3R,4R); 22.00 min (3R,4S).

Example 4d d) In an analogous manner to Example 4c 0.32 g 3-(4-cyclopentylmethyl-5-oxo-2,5-dihydro-furan-3ylmethyl)-1, 5,5-trimethyl-imidazolidine-2,4-dione was hydrogenated with a solution of 5.5 mg [Rh(COD)$_2$]SbF$_6$ and 5.8 mg (R)-3,5-iPr-MeOBIPHEP in 3.2 ml ethylacetate in a 35 ml stirred stainless steel autoclave at 80° C. and 100 bar hydrogen pressure The brown hydrogenation mixture was rotary evaporated. According to HPLC analysis as described in Example 4c the remainder contained 85% (3R,4R)-3-(4-cyclopentylmethyl-5-oxo-tetrahydrofuran-3ylmethyl)-1,5,5-trimethyl-imidazolidine-2,4-dione having an ee of 98%.

Example 4e e) In a manner analogous to Examples 4c and 4d the following hydrogenations were performed with 3-(4-cyclopentylmethyl-5-oxo-2,5-dihydro-furan-3ylmethyl)-1,5,5-trimethyl-imidazolidine-2,4-dione and the following results were obtained (Table 1) with ligands L and anions of a oxygen or complex acid A. HPLC analysis to determine the ee was performed as described in 4c before.

TABLE 1

| L | A | Solvent | S/C | T °C. | Press bar | Conv./h | ee % |
|---|---|---|---|---|---|---|---|
| (R)-MeOBIPHEP | SbF$_6$ | CH$_2$Cl$_2$ | 10 | 80 | 100 | 97/22 | 97 |
| (R)-MeOBIPHEP | BARF[4] | CH$_2$Cl$_2$ | 10 | 80 | 100 | 84/22 | 96 |
| (R)-MeOBIPHEP | BF$_4$ | CH$_2$Cl$_2$ | 10 | 80 | 100 | 33/22 | 95 |
| (R)-MeOBIPHEP | OTf | EtOAc | 100 | 80 | 100 | 42/18 | 98 |
| (R)-3,5-tBu$_2$-MeOBIPHEP | SbF$_6$ | THF | 200 | 80 | 100 | 71/18 | 97 |
| (R)-3,5-tBu$_2$-MeOBIPHEP | SbF$_6$ | EtOAc | 200 | 80 | 100 | 96/18 | 98 |
| (R)-MeOBIPHEP | BARF | CO$_2$sc[1] | 100 | 90 | 100 | 95/18 | 97 |
| (R)-MeOBIPHEP | BF$_4$ | CO$_2$sc[2] | 100 | 90 | 100 | 67/18 | 97 |
| (R)-3,5-iPr-MeOBIPHEP | SbF$_6$ | CO$_2$sc/EtOAc[3] | 1000 | 90 | 100 | 80/18 | 98 |
| (R)-3,5-tBu$_2$-MeOBIPHEP | SbF$_6$ | EtOAc | 100 | 120 | 80 | 91/19 | 96 |
| (R)-3,5-tBu$_2$-MeOBIPHEP | SbF$_6$ | EtOAc | 500 | 100 | 40 | 70/18 | 97 |
| (R,S)-pCF$_3$-PPF-PPh$_2$[5] | SbF$_6$ | EtOAc | 20 | 80 | 100 | 95/18 | 85 |
| (R,S)-PPF-P(tBu)$_2$[5] | SbF$_6$ | EtOAc | 20 | 80 | 100 | 97/18 | 87 |
| (R,R)-MeDUPHOS[5] | BF$_4$ | EtOAc | 10 | 60 | 100 | 27/64 | 80 |
| (R)-BIPHEMP | SbF$_6$ | EtOAc | 20 | 80 | 100 | 96/18 | 98 |
| (R)-BINAP | SbF$_6$ | EtOAc | 500 | 90 | 100 | 26/66 | 98 |
| (R)-2-Furyl-MeOBIPHEP | SbF$_6$ | EtOAc | 20 | 80 | 100 | 51/18 | 92 |
| (R)-3,5-iPr-MeOBIPHEP | SbF$_6$ | EtOAc | 500 | 90 | 100 | 97/18 | 98 |
| (R)-2-Naphthyl-MeOBIPHEP | SbF$_6$ | EtOAc | 500 | 90 | 100 | 18/19 | 98 |
| (R)-TriMeOBIPHEP | SbF$_6$ | EtOAc | 500 | 90 | 100 | 18/35 | 97 |
| (R)-3,4,5-MeO-MeOBIPHEP | SbF$_6$ | EtOAc | 500 | 90 | 100 | 18/36 | 97 |
| (R)-3,5-Me,4-MeO-MeOBIPHEP | SbF$_6$ | EtOAc | 500 | 90 | 100 | 18/87 | 97 |

[1])Solvent: 10 g CO$_2$; [2])Solvent: 12 g CO$_2$; [3])Solvent: 10 g CO$_2$ + 0.5 mL EtOAc; [4])BARF: B(3,5-(CF$_3$)$_2$—C$_6$H$_3$)$_4$; [5])These ligands are not atropisomeric ligands but also yield the (3R,4R) product.

Example 5

(2R,3R)-3-(3-Cyclopentylmethyl-2-hydroxymethyl-4-oxo-4-piperidin-1-yl butyl)-1,5,5-trimethyl-imidazolidine-2,4-dione To a suspension of 8.3 g AlCl$_3$ in 75 ml dichloromethane were added 12.3 ml piperidine at r.t. over 15 minutes. To the resultant clear, yellowish solution were added 16.8 g (3R,4R)-3-(4-cyclopentylmethyl-5-oxo-tetrahydrofuran-3ylmethyl)-1,5,5- trimethyl-imidazolidine-2,4-dione dissolved in 25 ml dichloromethane at r.t. over 30 minutes. After additional stirring at r.t. for 90 minutes, the reaction mixture was hydrolysed with 25 ml 1N HCl. The aqueous layer was extracted with dichloromethane and both organic layers were washed sequentially with 10% brine. After drying over Na$_2$SO$_4$ the combined organic layers were evaporated to yield 21.8 g viscous oil. The oily residue was dissolved in 150 ml diisopropyl ether at 50°, cooled down and stirred over night at −20°. After filtration, the crystals were washed with cold diisopropyl ether and dried in vacuum to yield 17.5 g (85.7%) slightly beige (2R,3R)-3-(3-cyclopentylmethyl-2-hydroxymethyl-4-oxo-4-piperidin-1-yl-butyl)-1,5,5-trimethyl-imidazolidine-2,4-dione; mp. 92–95° C.; $[\alpha]_{365}$=−5.6° (CHCl$_3$; c=1).

C$_{22}$H$_{37}$N$_3$O$_4$ (407,555) Calcd. C, 64.84; N, 9.15; N, 10.31. Found C, 64.94; H, 9.11; N, 10.30.

Example 6

(2R,3R)-3-Cyclopentylmethyl-4-oxo-4-piperidin-1-yl-2-(3,4,4-trimethyl-2,5-dioxo imidazolidin-1-ylmethyl)-butyric acid 20.4 g (2R,3R)-3-(3-Cyclopentylmethyl-2-hydroxymethyl-4-oxo-4-piperidin-1-yl-butyl)-1,5,5-trimethyl-imidazolidine-2,4-dione, 8.4 g NaHCO$_3$ and 5.9 g KBr were dissolved in 125 ml dichloromethane and 125 ml deionized water. After cooling down to 0°, 78 mg 2,2,6,6-tetramethyl-piperidin-1-oxyl (TEMPO) were added all at once and 107.4 g 9.90% aqueous sodium hypochlorite were added under vigorous stirring at 0° over 1 h. After additional stirring at 0° for 3 h the reaction mixture was acidified with 30 ml 6N HCl and the excess of the NaOCl was destroyed with 14 ml 38% aqueous sodium bisulfite. The aqeous layer was extracted with dichloromethane and both organic layers were washed with 10% brine. After drying over Na$_2$SO$_4$ the combined organic layers were evaporated to yield 21.8 g foam. The foamy residue was dissolved in 40 ml ethyl acetate at 500 and seeded with pure (2R,3R)-3-cyclopentylmethyl-4-oxo-4-piperidin-1-yl-2-(3,4,4-trimethyl-2,5-dioxo imidazolidin-1-ylmethyl)-butyric acid. 40 ml Hexane were then added under stirring over 1 h while cooling down to r.t. The suspension was stirred for 1 h at 0° and at −20° over night. After filtration, the crystals were washed with hexane and dried in vacuum to yield 17.6 g (83%) off-white (2R,3R)-3-cyclopentylmethyl-4-oxo-4-piperidin-1-yl-2-(3,4,4-trimethyl-2,5-dioxo imidazolidin-1-ylmethyl)-butyric acid; mp. 111–114°. $[\alpha]_D$=−41.6° (CHCl$_3$; c=1)

C$_{22}$H$_{35}$N$_3$O$_5$ (421,538) Calcd. C, 62.69; H, 8.37; N, 9.97. Found C, 62.35; H, 8.59; N, 9.93.

Example 7

(2R,3R)-3-Cyclopentylmethyl-N-hydroxy-4-oxo-4-piperidin-1-yl-2-(3,4,4-trimethyl-2,5-dioxo-imidazolidin-1-ylmethyl)-butyramide 0.78 g of 2-morpholino-ethyl isocyanide was added at 220 to a suspension of 2.11 g of the product of Example 6 and 0.61 g of N-hydroxy-2-pyridone in 21 ml of methylene chloride and the mixture was stirred for 3 h. The solution was treated with 0.58 g of 0-trimethylsilylhydroxylamine and stirred for 2 h. The reaction mixture was washed with saturated NaHCO$_3$ solution and with water and evaporated. The residue was dissolved in 20 ml of t-butyl methyl ether and 0.23 ml of water, stirred for 1½ h. at 220, the suspension was diluted with 10 ml of hexane, filtered and the residue was dried at 22°/11 mbar, there being obtained 1.82 g (83%) of pure (2R,3R)-3-cyclopentylmethyl-N-hydroxy-4-oxo-4-piperidin-1-yl-2-(3,4,4-trimethyl-2,5-dioxo-imidazolidin-1-ylmethyl)-butyramide MS (EI): 436 (40%).

What is claimed is:

1. A process for producing a compound of formula (IV)

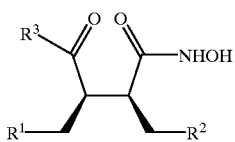
(IV)

wherein R¹ is lower alkyl or lower cycloalkyl; R² is a 5- or 6-membered N-heterocyclic ring wherein (a) the ring is covalently bonded to the remainder of the compound via a linking N atom, (b) the ring contains 0, 1 or 2 additional hetero groups as ring members, selected from the group consisting of N, O and/or S, SO or $SO_2$, (c) both ring atoms adjacent to the linking N atom are C, one or both of which are substituted by oxo, (d) the ring is either optionally benz-fuzed or optionally substituted by lower allyl or oxo on one or more C atoms non-adjacent to the linking N atom; (e) the ring is optionally substituted by lower alkyl on one or more N atom(s) non-adjacent to the linking N atom by lower alkyl; and R³ is a saturated 5- to 7-membered monocyclic N-heterocyclic ring which is attached to the remainder of the compound of formula IV via the N-atom and optionally contains one additional hetero group selected from NR⁴ and O as a ring member; and R⁴ is hydrogen, lower alkyl, aryl, aralkyl or a protecting group, comprising:

a) reacting a compound of formula (I)

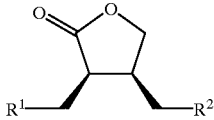
(I)

with a cyclic amine HR³ yielding a compound of formula (V)

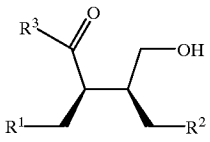
(V)

b) oxidizing the hydroxyl group in a compound of formula (V) yielding a compound of formula VI

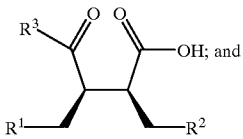
(VI)

c) introducing a hydroxyl amine at the hydroxyl of the compound of formula (VI), yielding the compound of formula (IV).

2. The process of claim 1, wherein the compound of formula IV contains the hetero group NR⁴ and R⁴ is a protecting group, further comprising cleaving R⁴.

3. The process according to claim 1 wherein R¹ is cyclopentyl, R² is 3,4,4-Trimethyl-2,5-dioxo-imidazolidin-1-yl and R³ is piperidine.

4. A compound of formula V

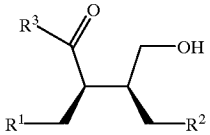
(V)

wherein R¹, R² and R³ are as defined in claim 1.

5. The compound of claim 4, (2R,3R)-3-(3-Cyclopentylmethyl-2-hydroxymethyl-4-oxo-4-piperidin-1-yl butyl)-1,5,5-trimethyl-imidazolidine-2,4-dione.

* * * * *